(12) United States Patent
Milbocker et al.

(10) Patent No.: US 12,083,005 B2
(45) Date of Patent: Sep. 10, 2024

(54) MICROSTRUCTURED SOFT TISSUE GRAFT

(71) Applicant: BVW Holding AG, Cham (CH)

(72) Inventors: Michael Milbocker, Holliston, MA (US); Lukas Bluecher, Eurasberg (DE)

(73) Assignee: BVW Holding AG, Cham (CH)

( * ) Notice: Subject to any disclaimer, the term of this patent is extended or adjusted under 35 U.S.C. 154(b) by 365 days.

(21) Appl. No.: 17/392,373

(22) Filed: Aug. 3, 2021

(65) Prior Publication Data

US 2022/0039934 A1     Feb. 10, 2022

Related U.S. Application Data

(60) Provisional application No. 63/061,166, filed on Aug. 4, 2020.

(51) Int. Cl.
| | |
|---|---|
| *A61F 2/00* | (2006.01) |
| *D04H 1/72* | (2012.01) |
| *D04H 1/728* | (2012.01) |
| *D04H 1/74* | (2006.01) |

(52) U.S. Cl.
CPC ........... *A61F 2/0063* (2013.01); *D04H 1/728* (2013.01); *D04H 1/74* (2013.01); *A61F 2002/0068* (2013.01); *A61F 2210/0004* (2013.01); *A61F 2240/001* (2013.01); *D10B 2321/022* (2013.01); *D10B 2509/00* (2013.01)

(58) Field of Classification Search
CPC ........... A61F 2/0063; A61F 2002/0068; A61F 2210/0004; A61F 2240/001; D04H 1/728; D04H 1/74; D10B 2321/022; D10B 2509/00
See application file for complete search history.

(56) References Cited

U.S. PATENT DOCUMENTS

| | | | |
|---|---|---|---|
| 8,389,114 B2 | 3/2013 | Luzinov et al. | |
| 9,120,670 B2 | 9/2015 | Hulseman et al. | |
| 9,908,274 B2 | 3/2018 | Hulseman et al. | |
| 9,988,201 B2 | 6/2018 | Darin et al. | |
| 10,377,044 B2 | 8/2019 | Hulseman et al. | |
| 10,458,053 B2 | 10/2019 | Hulseman et al. | |
| 10,575,667 B2 | 3/2020 | Hulseman et al. | |

(Continued)

FOREIGN PATENT DOCUMENTS

WO     2019079622 A1     4/2019

OTHER PUBLICATIONS

International Search Report for corresponding patent application No. PCT/US2021/044331, dated Oct. 29, 2021, 14 pages.

*Primary Examiner* — Jing Rui Ou
(74) *Attorney, Agent, or Firm* — Patterson Intellectual Property Law, P.C.; Ryan D. Levy; Mark A. Kilgore

(57) ABSTRACT

The present disclosure comprises micropatterned fabric, meshes, textiles, and implantable devices which may include having one substrate including a mesh, a second substrate having a microstructured surface, and a fibrous layer disposed therebetween. The fibrous layer comprises a plurality of randomly oriented fibers. The devices having the microstructured surface may include a plurality of first level microfeatures and a plurality of second level microfeatures wherein the plurality of second level microfeatures are disposed hierarchically the first level microfeatures. Also disclosed are methods for making such micropatterned fabric, meshes, textiles, and implantable devices.

20 Claims, 5 Drawing Sheets

(56) References Cited

U.S. PATENT DOCUMENTS

| | | |
|---|---|---|
| 10,687,642 B2 | 6/2020 | Hulseman et al. |
| 10,889,005 B2 | 1/2021 | Hulseman et al. |
| 2013/0317286 A1 | 11/2013 | Bluecher et al. |
| 2014/0148827 A1* | 5/2014 | Odermatt ............ A61B 17/0057 606/151 |
| 2014/0257348 A1* | 9/2014 | Priewe .................. A61F 2/0063 606/151 |
| 2014/0257517 A1* | 9/2014 | Deichmann ............. B29C 70/68 623/23.74 |
| 2015/0305739 A1* | 10/2015 | Rolandi ................. A61B 17/08 606/221 |
| 2015/0368838 A1 | 12/2015 | Hulseman et al. |
| 2017/0014111 A1 | 1/2017 | Hulseman et al. |
| 2018/0236511 A1* | 8/2018 | Milbocker .......... B81C 1/00206 |
| 2019/0062155 A1 | 2/2019 | Hulseman et al. |
| 2019/0117849 A1* | 4/2019 | Bluecher ................ A61L 31/06 |
| 2020/0155292 A1* | 5/2020 | Bluecher ............... A61L 31/022 |
| 2020/0338808 A1 | 10/2020 | Hulseman et al. |
| 2021/0086371 A1 | 3/2021 | Hulseman et al. |

\* cited by examiner

MICROSTRUCTURED SOFT TISSUE GRAFT

CROSS-REFERENCES TO RELATED APPLICATIONS

This application claims benefit of the following patent application(s) which is/are hereby incorporated by reference: U.S. Provisional Application No. 63/061,166 filed on Aug. 4, 2020

A portion of the disclosure of this patent document contains material that is subject to copyright protection. The copyright owner has no objection to the reproduction of the patent document or the patent disclosure, as it appears in the U.S. Patent and Trademark Office patent file or records, but otherwise reserves all copyright rights whatsoever.

STATEMENT REGARDING FEDERALLY SPONSORED RESEARCH OR DEVELOPMENT

Not Applicable

REFERENCE TO SEQUENCE LISTING OR COMPUTER PROGRAM LISTING APPENDIX

Not Applicable

BACKGROUND

The present invention relates generally to micropatterned fabric, meshes, textiles, and the like. More particularly, this disclosure pertains to devices of, and methods for creating, a substrate having disposed thereon a micropattern wherein the substrate is capable of generating adhesive force to a target surface.

Implantable devices for repairing soft tissue defects generally suffer from migration issues. Consequently, such devices, such as prosthetics, are generally sutured or tacked to the tissue surrounding the defect to limit the movement of the device from the target location. While the mechanical means of sutures or staples are efficient at limiting movement of the device from the target location, attaching a prosthetic to healthy tissue results in trauma to the tissue. The cascade of effects from this trauma can lead to post-surgery adhesions which can cause further complications and pain to a patient. The time required to position and attach the prosthetic considerably increases the time required to complete the procedure. Such prosthetics generally have no adhesive properties, and consequently the prosthetic is likely to move in the time interval between initial positioning of the prosthetic and the fixation of the prosthetic to the tissue. As an even further downside, the lack of an adhesive property to these prosthetics makes implanting them through minimally invasively procedures, such as laparoscopically, particularly difficult, rendering them nearly unusable for such procedures.

What is needed, then, is a soft tissue repair device which has adhesive properties, can be fixated without the need for sutures or other mechanical means which cause trauma, and provides post-surgical prevention of complications such as adhesions or other trauma-related issues.

BRIEF SUMMARY

In certain embodiments disclosed herein, an adhesive component may be added to a soft tissue repair fabric. In some embodiments, the soft tissue repair fabric may be a surgical mesh. The adhesive component may include an interwoven absorbable matrix applied to a mesh with fibers protruding out of the plane of the mesh. The added fibers may considerably increase the mass and rigidity of the implantable fabric. In some embodiments, an implantable surgical mesh may be generally dependent on the fibers for providing mesh strength. In certain embodiments, the fibers may also be ornamented with an adhesive microstructure that provides a distinct clinical advantage compared to a composite structure. Composite soft tissue repair fabrics comprise a first reinforcement component and a second anti-slip component. For example, one of the composite soft tissue repair fabrics may be a sheet of adhesive microstructure bonded to a standard polypropylene mesh. The sheet component is often quite rigid and defeats the flexible aspect of a woven mesh making the tissue repair fabric stiffer and less pliant.

Consequently, there is a need for a soft tissue repair fabric which is compliant, strong, and comprises a minimum amount of material weight.

There is also a need for a soft tissue repair fabric which self-adheres to a target tissue surface and is sufficiently pliant to avoid creation of gaps between the implantable fabric and the target tissue surface. A self-adherent aspect of the present disclosure may be described through capillary action or may be through the establishment of a Wenzel-Cassie interface between the implantable fabric and the target tissue surface.

There is a need for an implant having a microsurface texture which is capable of creating an immediate Wenzel-Cassie adhesion that immobilizes the implant. In some embodiments, this same microsurface texture may further promote healthy integration of the implant with the surrounding tissue. Wenzel-Cassie adhesion may occur by the formation of phase domains in the interface between the implant surface and the tissue surface. This type of adhesion may form an interface layer between tissue and the implant. Unexpectedly, the applicants have discovered that the formation of Wenzel-Cassie zones of adhesion are stronger than frictional interfaces.

In some embodiments, a hierarchical structure as disclosed herein may include an assembly with a multi-scale morphology and with a large and accessible surface area. Recent advances in nanomaterial science have made increasingly possible the design of hierarchical microstructured surfaces with specific properties. Most of this work has concentrated on hierarchical single-walled carbon nanotube films realized by a simple, rapid, reproducible, and inexpensive filtration process from an aqueous dispersion. By varying the thickness of carbon nanotube random networks, it is possible to adapt their wettability due to capillary phenomena in the porous films.

In some embodiments, a hierarchical microstructured surface may be a surface microstructure comprising high surface energy regions juxtaposed with lower surface energy regions. These high and low surface energy regions need not be stacked, but rather be in juxtaposition to each other. Typically, higher Wenzel-Cassie localization forces are achieved when the microstructures span a three-dimensional space and are stacked.

High surface energy microstructures are considered to be wetting, and in the case of water wetting high surface energy microstructures are said to be hydrophilic. Low energy microstructures are considered to be non-wetting, and in the case of water wetting low surface energy microstructures are said to be hydrophobic. The combination of wetting and non-wetting zones in juxtaposition creates what is known as a Wenzel-Cassie interface.

It will be understood that the Wenzel-Cassie interface does not require an outward radial force to create a localizing force. In order to translate the implantable surface relative to the target surface requires adding energy to disrupt the low energy state of the Wenzel-Cassie interface. In some embodiments, the hierarchical microstructured surface has a low contact area with the target surface, and in some embodiments, no contact at all.

Certain embodiments of the present disclosure may include microstructured surfaces that have a periodicity. This periodicity may create second-order Wenzel-Cassie interfaces, which here are considered as Wenzel-Cassie interfaces. A second-order Wenzel-Cassie interface is characterized as some type of mechanical deformation of the target surface and/or microstructured surface which creates an interlocking condition between the microstructured surface and target surface wherein the deformation is caused by mostly non-frictional forces.

For example, in some embodiments, a target surface may possess an eigenwrinkle mode(s) of deformation which causes wrinkling of the target surface without mechanical damage occurring to the target surface. These wrinkles can be matched to one or more periodicities of the microstructured surfaces such that the target surface and microstructure surface may interlock with minimal mechanical contact. Alternatively, the microstructured surface may also possess an eigenwrinkle mode(s), which can achieve the same second-order Wenzel-Cassie effect. In essence, shear forces may be translated into wrinkling of either the implantable surface or tissue surface without displacement of the implant.

In some embodiments, a related, but different second-order Wenzel-Cassie effect may be associated with Schallamach waves. These waves are generated in either the microstructure surface or the target surface, and comprise multiple wrinkle components, some of which may not be eigenmodes. The periodicity of the microstructured surface may "catch" some components of the Schallamach waves and allows other components to "pass by." A second-order Wenzel-Cassie interface of this type is referred to herein as a "slip-grip" interface.

Other second and third order Wenzel-Cassie interfaces may also be employed, where the Wenzel-Cassie interface and the periodicity of the microstructured surface work in cooperation to localize an implant placed on a dynamically changing target surface. The spatial periodicity of the microstructure may be coupled cooperatively with other mechanical properties of the microstructures surface, for example, the Young's modulus of the material comprising the microstructured surface. Additionally, the geometry of the microstructured surface and how it is attached to the implant can enhance or diminish these second order Wenzel-Cassie effects.

The soft tissue repair devices of the present invention may be characterized by mechanical properties that are unlike any implants/prosthetics currently disclosed in the prior art. Microstructured surfaces employing hydrophobic and hydrophilic regions may yield devices that exhibit displacement forces that increase when the target contact surface/lumen becomes wet, when oil is applied, when a surfactant is applied, or when a lubricant is applied. This physical characteristic of enhanced grip under conditions which generally decrease grip is the opposite result of implants/prosthetics found in the prior art which are generally populated with mechanical friction surface texture. The issue with implants/prosthetics of the prior art is that generally the in vivo environment tends to lubricate the surface of the devices and prevent frictional resistance to migration.

For frictional treatments of the prior art, such as including barbs, raised struts, surface cylinders, pyramids and the like to be effective, large radial forces must be supplied in order for the interpenetration between tissue and surface frictional geometry to be effective. Conversely, in embodiments of the present disclosure, the Wenzel-Cassie zones created by the microstructure when wet may prevent migration through a variety of non-contact effects broadly called Van Der Waals forces. These localization forces may largely be characterized as electronic and quantum mechanical rather than mechanical and classical.

In some embodiments, the Wenzel-Cassie effect may create a "suck down" effect between the target surface and the implant device. Thus, rather than outward radial forces applied to the tissue, inward (suctional) radial forces may be applied.

While these novel effects detail some aspects of various embodiments of this disclosure, one should not exclude combinations of Wenzel-Cassie effects and mechanical frictional effects, especially in applications where one is preferred over the other on discrete portions of the same device In some additional embodiments, adhesive and lubricious microsurface textures may be used in combination. Fluid thinning and fluid thickening are common effects due to the disordering or ordering of water molecules, respectively, caused by the effect the microstructured surface's spatially distributed surface energy patterns have on the electric dipoles in the interfacial fluid. In particular, regions of high surface energy may be juxtaposed with regions of low surface energy to cause tissue dynamics to pass through the implant device without displacing it. These, and other effects will be described in detail below.

There is also a need for a soft tissue repair fabric which can be repositioned peri-operatively without damaging the tissue the prosthetic contacts.

There is also a need for a soft tissue repair fabric with improved resistance to migration. In particular, there is a need for a soft tissue repair fabric which does not require suture, tacks, or other mechanical mechanisms between the fabric and target surface to prevent post-operative device migration.

There is also a need for a soft tissue repair fabric with minimal areal density (mass per unit area) and maximal tensile strength.

Additionally, various methods for texturizing or producing patterned effects in fabrics are generally known. Texturizing methods include chemical methods, such as, chemical etching, localized shrinking techniques, and physical methods, such as, mechanically cutting, compressing, or compacting areas of the fabric.

In some embodiments, the soft tissue repair fabric may include a mesh, an interfacial web structure, and an embossed microstructure. The microstructure can be embossed on a prepolymer layer on the interfacial web or embossed directly on the interfacial web by heating.

In a third embodiment, a standard polymeric mesh may be internally heated to a deformable state, whereupon a microstructure is then embossed. The polymeric mesh material is heated uniformly and nondestructively, such that the original tensile strength of the mesh is retained after the microstructure is embossed on the fibers comprising the mesh.

By means of the present disclosure, highly adhesive and hierarchical patterned effects may be obtained on a medical prosthetic at relatively low processing costs.

BRIEF DESCRIPTION OF THE SEVERAL VIEWS OF THE DRAWINGS

FIG. 5B is a detailed illustration of a fluted microstructure.

DETAILED DESCRIPTION

Figure 2:
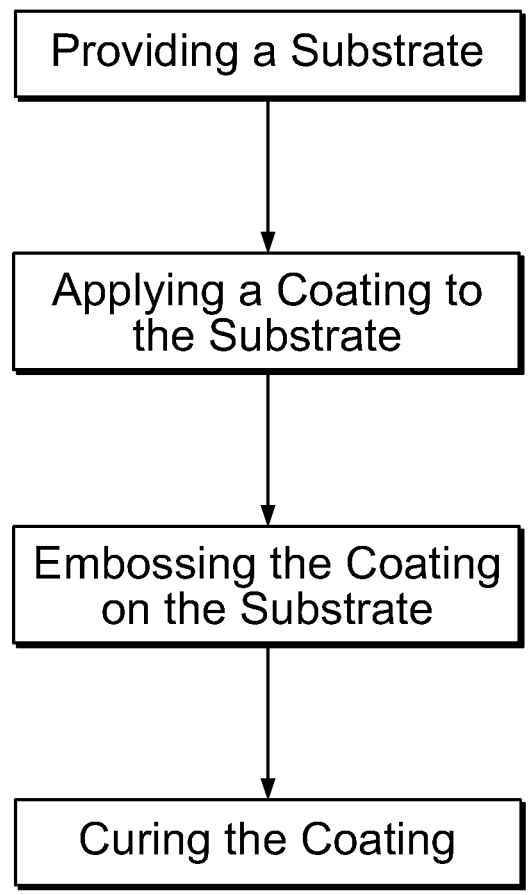
FIG. 2 is a flow chart of a method for creating an embodiment of the present disclosure

Referring to FIG. 2, a method for producing a substrate having a micropattern disposed thereon is disclosed. In some embodiments, the method may include providing a substrate. The substrate may comprise a material suitable for being coated. In certain embodiments, the substrate may be a type of material such as fabric, plastic, polymer, and the like. In certain embodiments, the material may be biocompatible, bioabsorbable, biostable, nonresorbable, or the like, and may be combinations thereof. In some embodiments, a substrate may include at least one portion that is bioabsorbable and a second portion that is nonresorbable. In other embodiments, a substrate may be biocompatible, and include one portion that is bioabsorbable and a second portion that is nonresorbable. In certain embodiments, a substrate may comprise more than one material that is combined together, where each component may be fabric, plastic, polymer or the like, and may be biocompatible, bioabsorbable, biostable, nonresorbable, or the like, and may be combinations thereof.

In some embodiments, a coating of a polymeric adhesive or binder may be applied to the substrate. The coated substrate may then undergo embossing. In certain embodiments, a mold or embossing surface may be applied to the coated substrate via a physical embossing structure, such as a cylindrical roller or stamping press. In some embodiments, the coated substrate with embossing may be cured.

In some embodiments, the coating may be in a liquid state when undergoing the embossing step. In certain embodiments, the coating may be in a semi-liquid/semi-solid state when undergoing the embossing step. In certain embodiments where the coating is in a liquid state when undergoing embossing, the coating may be transferred through a rotating cylindrical mold for embossing. In certain embodiments, the mold for the embossing process may be embodied in a cylindrical screen which can rotate simultaneously with the movement of the substrate thereunder.

Figure 1:
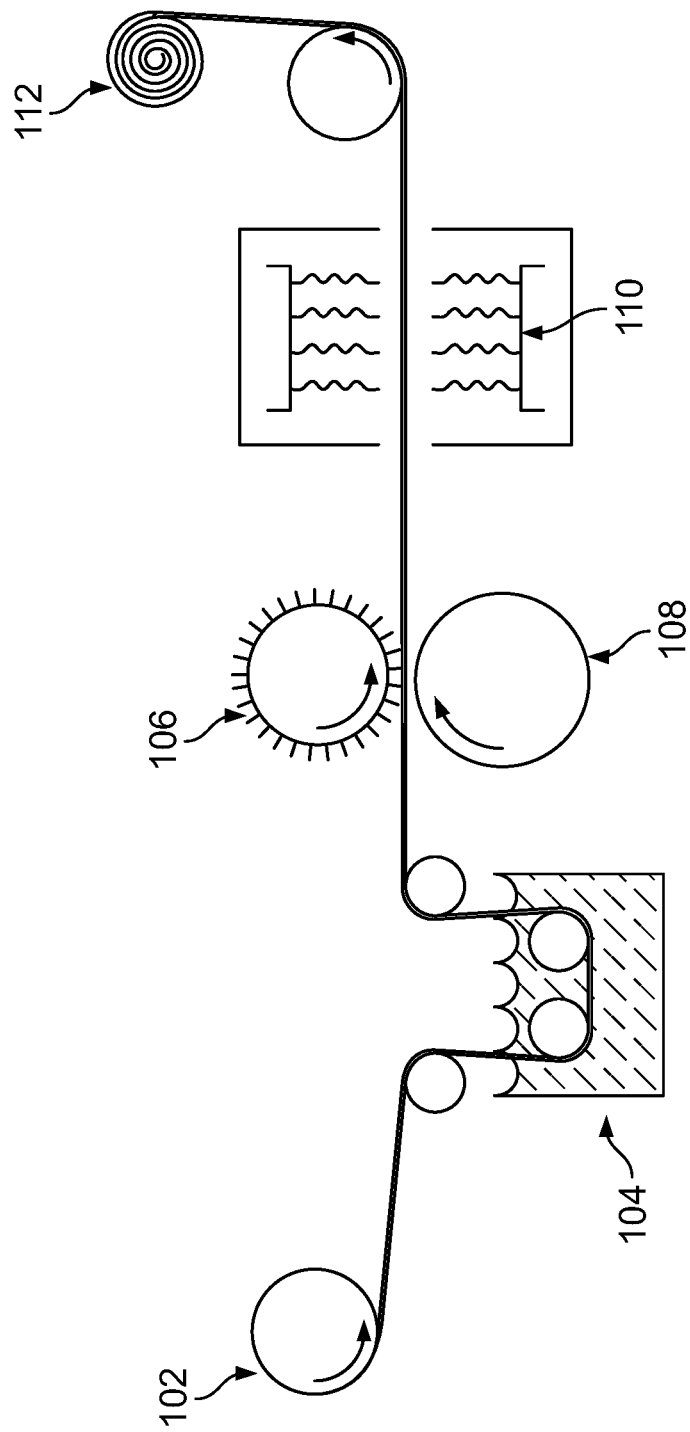
FIG. 1 is an illustration of a method for creating an embodiment of the present disclosure.

Referring to FIG. 1, a method of producing a substrate having a micropattern disposed thereon may include a roller of substrate material 102. In some embodiments the roller 102 may provide a continuous source of substrate material as it is unwound. The substrate material may be transferred to a second area where a coating may be applied. In some embodiments, the coating may be a polymeric adhesive or binder. In certain embodiments, the coating may be applied via a dipping station 104. In other embodiments, the coating may be spray applied or applied via electrostatic discharge. In some embodiments, after coating, the coated substrate may pass through cylindrical embossing roller 106. In certain embodiments, the cylindrical embossing roller 106 may include a mold having microstructured pattern which may be transferred to the coating. In some embodiments, the mold may be a positive mold. In some embodiments, the mold may be a negative mold. In some embodiments, the mold may include both positive and negative portions of the mold. In certain embodiments, the embossing process may include a contact pressure cylinder 108 for applying pressure to the coated substrate in contact with the cylindrical embossing roller 106. In some embodiments, gas pressure may be applied rather than the contact pressure cylinder 108.

In embodiments that utilize gas pressure, the gas may be directed onto the surface of the mold to press the mold against the coated substrate, or the gas may be directed against the coated substrate to press the coated substrate against the mold.

After the coating is embossed with a microstructured pattern, the microstructured substrate may be passed through a curing process 110. The curing process may be one of the conventional types known in the art wherein the coating is set or cured. In some embodiments, the microstructured substrate may then be collected for storage or for further processing. In some embodiments, the microstructured substrate may be wound into a roll of material 112.

In certain embodiments as disclosed herein, the coating disposed on the substrate may generally be classified as a water-based and/or a solvent-based coating. In some embodiments, a water-based coating may consist of one or more of the following: a binder, an emulsion polymer, and/or a viscosity builder, or any combination thereof. In certain embodiments, the water-based coating may include a binder, emulsion polymer and viscosity builder all together. In other embodiments, they may also contain one or more of the following: plasticizers, thermosetting resins, curing catalysts, stabilizers and/or other additives.

The emulsion polymers may be selected from the following: acrylic, vinyl-acrylic, vinyl, urethane and/or styrene butadiene latexes, and combinations thereof. In embodiments where the coating is cured, it may be generally necessary to increase the viscosity of the coating to about 30,000 to 100,000 MPa-s (millipascal-seconds) immediately after embossing so that the microstructure maintains the desired geometry between embossing and curing. In certain embodiments, the viscosity may be dictated, at least in part, by the nature of the substrate and/or the method of contacting the microstructure with the coating layer.

Suitable thickeners for increasing viscosity may include water soluble polymers such as carboxymethyl cellulose, hydroxyethyl cellulose, polyoxymethylene, and natural gums as well as alkali swellable polymers such as highly carboxylated acrylic emulsion polymers and poloxamer prepolymers.

In some embodiments, plasticizers may be added to alter the feel of the finished goods or to improve the flow and leveling characteristics of the coatings. Where one goal is to improve leveling characteristics, fugitive plasticizers such as the phthalate esters may be employed. If one goal is to alter the tactile feel of the finished device or at least a portion of the finished device, then more permanent plasticizers such as low molecular weight polyesters may be used.

In some embodiments, thermosetting resins such as methylol-melamines, urea formaldehyde condensates, or phenol-formaldehyde condensates may be incorporated to improve durability or abrasion resistance of the finished device.

In certain embodiments which include a catalysts, oxalic acid or diammonium phosphate may be used. In some embodiments, the use of a catalyst may increase the rate of cure of the adhesive. More specialized additives may be used which may include ultraviolet absorbers where the backing, such as urethane foam, is subject to photo degradation and dyes or pigments to impart a color to the adhesive layer. When a breathable film is desired, coatings may be chemically or mechanically foamed. Solvent coatings may include both fully reacted soluble polymers such as acrylic homo- and co-polymers, polyesters, polyamides, or polyurethanes.

Solvent coatings may also include both fully reacted soluble polymers such as acrylic homo- and co-polymers, polyesters, polyamides, or polyurethanes and two part systems such as polyester polyols with diisocyanates or isocyanate prepolymers and epoxies with polyamines.

The polymer or prepolymer may be dissolved in a suitable solvent which is preferably low boiling, and then thickened to the proper viscosity in a manner similar to that used for water-based adhesives. In some embodiments of the solvent-based coatings, catalysts, crosslinking agents, stabilizers, pigments, or dyes may also be incorporated.

Certain embodiments disclosed herein may incorporate cylindrical molds for embossing patterns onto the substrate, or onto the coating of the substrate. As disclosed previously, some embodiments may incorporate a contact pressure cylinder for applying pressure to the coated substrate in contact with the cylindrical embossing roller, and some embodiments may incorporate gas pressure rather than the contact pressure cylinder. In embodiments that use gas pressure, there may be a range of gas pressures that provide acceptable outcomes. In some embodiments, gas pressures may range from about 30 psi to about 100 psi. In certain embodiments, gas pressures may range from about 60 psi to 100 psi.

An embodiment of a cylindrical mold may include a substrate or coated substrate resting on and being conveyed by a conveyer belt or similar transportation system. In some embodiments, the conveyor belt may include positioning holders which project upward therefrom for the purpose of maintaining the positioning of the substrate on the belt as well as maintain the substrate in a substantial flat position against the belt. Typically, the conveyor belt may be a tenter frame or a conventional type of conveyor belt or blanket, vacuum belt, etc., adapted to maintain the substrate in a flattened form. The conveyor may be wider than the substrate such that on either side of the substrate there may exist border regions between the outer edges of the substrate and the outer edges of the belt. In some embodiments, the cylindrical mold may be a rotary mold which rotates at the same speed, or approximately the same speed as the conveyor system. In some embodiments, the conveyor system and rotary mold may include wheels which rest on the border regions of the belt. The wheels may be of any type of suitable materials such as plastic, metal, rubber, etc. The cylindrical mold may include extensions which protrude through the wheels and rest on support brackets which are adapted for rotatable support of the mold.

Thus, by virtue of the support brackets, the bulk of the weight of the cylindrical mold may be supported by the brackets. In turn, the wheels may rest lightly on the border portions such that movement of the conveyor causes rotation of the cylindrical mold in the same direction as the substrate, while the axis of the cylindrical mold is maintained in a position substantially perpendicular to the direction of the conveyor movement. In other embodiments, the cylindrical mold may include support brackets which include integral, or external, rotation devices which rotate the cylindrical mold. The rotation of the cylindrical mold may coincide with the speed of the conveyor belt system.

Certain embodiments disclosed herein may include an implantable device for repairing soft tissue defects. In one embodiment, the device may include a surgical mesh with a laminate layer comprising a microstructure. In certain embodiments, a laminate-like structure may include a region having a soft, absorbent central core of relatively low fiber concentration that may be disposed between two strong, abrasion resistant surface regions.

Figure 3:
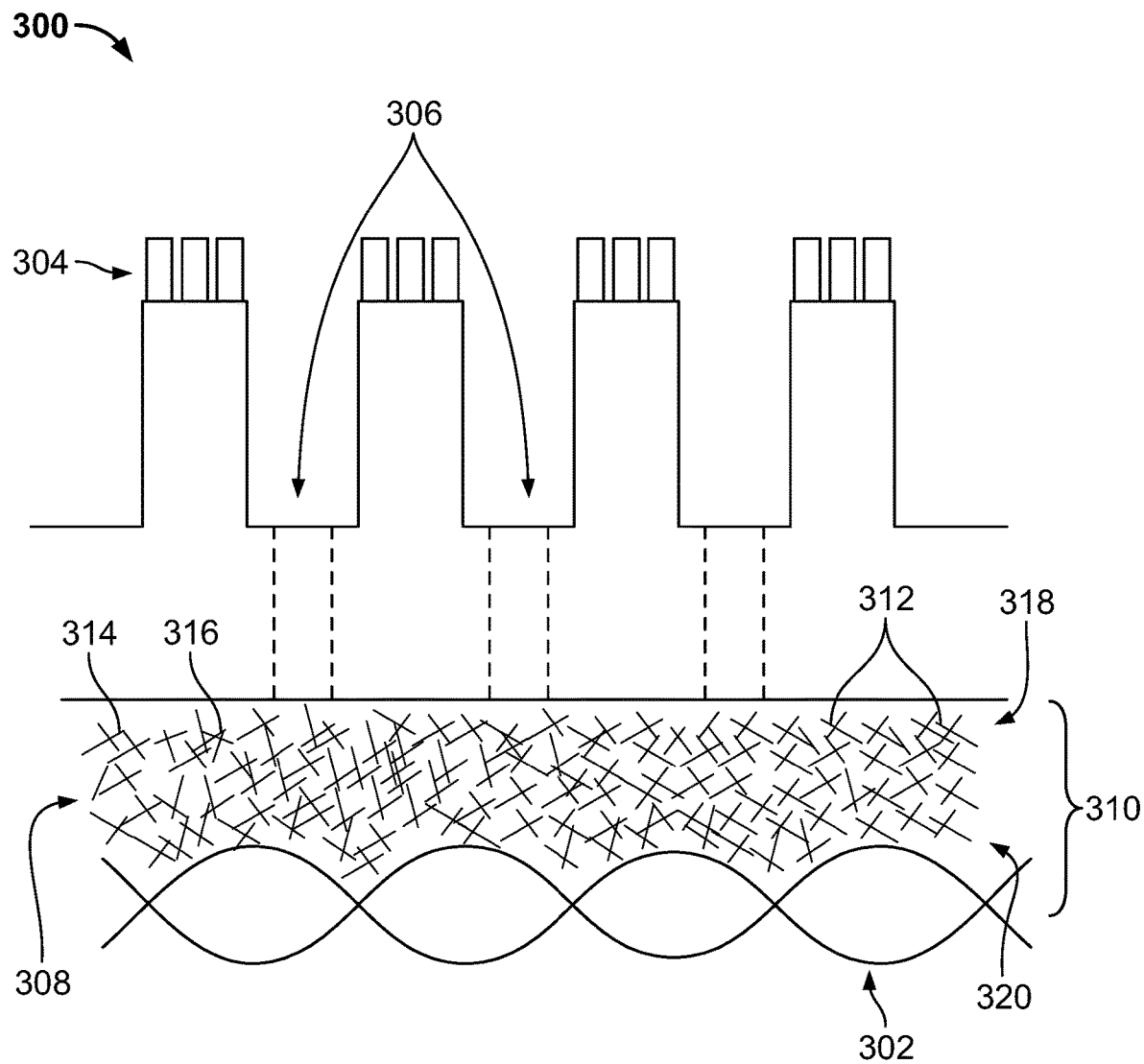
FIG. 3 is an illustration of one embodiment of a microstructured soft tissue device.

Referring now to FIG. 3, an implantable device 300 may include a mesh structure 302 and a substrate having a microstructured surface 304. In some embodiments, the microstructured surface may include a region 306 capable of generating capillary action. In certain embodiments, the capillary action region 306 may be in communication with a fibrous layer 308 residing between the microstructured surface 304 and the mesh surface 302. In certain instances, the capillary action may draw moisture into the fibrous of the fibrous layer 308. The relatively low fiber concentration within the central core region 310 provides space to increase the amount of moisture absorbable by the fibrous layer.

In some embodiments, within the central core region 310 are networks of fibers 312 generally connecting the two surface regions together without the use of bonding material or adhesives. In some embodiments, the use of bonding material or adhesives may be used but may not be disposed throughout the entire central core region 310. In certain embodiments, the bonding material in at least one surface region is disposed in a fine, spaced-apart pattern, and the bonded portions in that surface region are finely modeled to soften them. In other embodiments, the bonding material or adhesive may be used throughout the central core region. Generally, the bonding material or adhesive may be used to connect the two surface regions within the implantable device.

Certain embodiments, as disclosed herein, forming of a fibrous layer 308 may be accomplished in a variety of ways. In some embodiments, it may be preferable to form the fibrous layer 308 of randomly oriented short fibers 314, 316. In certain embodiments, the fibrous layer 308 may include a first side 318 to which is applied a first bonding material or adhesive which may penetrate the fibrous layer. In some embodiments, the penetration may occur from about 10 to about 60 microns through the thickness of the fibrous layer, or from about 10 microns to about 50 microns, from about 10 microns to about 40 microns, from about 10 microns to about 30 microns, from about 10 microns to about 20 microns, or from about 10 microns to about 15 microns. In other embodiments, the penetration of the first bonding material may occur from about 20 microns to about 50 microns, from about 30 microns to about 40 microns, or to about 35 microns. In yet other embodiments, the penetration may occur from about 20 microns to about 60 microns, from about 30 microns to about 60 microns, from about 40 microns to about 60 microns, or from about 50 microns to about 60 microns.

In some embodiments, the fibrous layer 308 may include a second side 320 to which is applied a second bonding material in a fine, spaced-apart pattern which penetrates from about 10 to about 60 microns through the thickness of the fibrous layer or from about 10 microns to about 50 microns, from about 10 microns to about 40 microns, from about 10 microns to about 30 microns, from about 10 microns to about 20 microns, or from about 10 microns to about 15 microns. In other embodiments, the penetration of the first bonding material may occur from about 20 microns to about 50 microns, from about 30 microns to about 40 microns, or to about 35 microns. In yet other embodiments, the penetration may occur from about 20 microns to about 60 microns, from about 30 microns to about 60 microns, from about 40 microns to about 60 microns, or from about 50 microns to about 60 microns. In some embodiments, the first bonding material and second bonding material do not contact one another in the thickness of the fibrous layer. In some embodiments, the first bonding material and second bonding material do not substantially contact or connect with each other, wherein substantially no contact or connection includes 10% or less contact area, 15% or less, 20% or less, 25% or less, 30% or less, 35% or less, 40% or less, 45% or less, or 50% or less.

In some embodiments, an implantable device may include applying bonding material in a fine, spaced-apart pattern to one side of the fibrous layer with the bonding material adhering the first side of the fibrous to the microstructured surface, and then repeating those steps to the second side of the fibrous layer and bonding the second side to a surgical mesh.

In some embodiments wherein a surgical mesh is used, the implantable device may include forming a fibrous layer, which may comprise randomly oriented short fibers 314, 316. In certain embodiments, the fibrous layer 308 may include a first side 318 to which is applied a first bonding material or adhesive which may penetrate the fibrous layer. In some embodiments, the penetration may occur from about 10 to about 60 microns through the thickness of the fibrous layer, or from about 10 microns to about 50 microns, from about 10 microns to about 40 microns, from about 10 microns to about 30 microns, from about 10 microns to about 20 microns, or from about 10 microns to about 15 microns. In other embodiments, the penetration of the first bonding material may occur from about 20 microns to about 50 microns, from about 30 microns to about 40 microns, or to about 35 microns. In yet other embodiments, the penetration may occur from about 20 microns to about 60 microns, from about 30 microns to about 60 microns, from about 40 microns to about 60 microns, or from about 50 microns to about 60 microns.

In some embodiments, the fibrous layer 308 may include a second side 320 to which is applied a second bonding material in a fine, spaced-apart pattern which penetrates from about 10 to about 60 microns through the thickness of the fibrous layer or from about 10 microns to about 50 microns, from about 10 microns to about 40 microns, from about 10 microns to about 30 microns, from about 10 microns to about 20 microns, or from about 10 microns to about 15 microns. In other embodiments, the penetration of the first bonding material may occur from about 20 microns to about 50 microns, from about 30 microns to about 40 microns, or to about 35 microns. In yet other embodiments, the penetration may occur from about 20 microns to about 60 microns, from about 30 microns to about 60 microns, from about 40 microns to about 60 microns, or from about 50 microns to about 60 microns. In some embodiments, the first bonding material and second bonding material do not contact one another in the thickness of the fibrous layer. In some embodiments, the first bonding material and second bonding material do not substantially contact or connect with each other, wherein substantially no contact or connection includes 10% or less contact, 15% or less, 20% or less, 25% or less, 30% or less, 35% or less, 40% or less, 45% or less, or 50% or less. In some embodiments, the second side 320 may then be adhered to a surgical mesh with the second bonding material. In some embodiments, the first side 318 may be adhered to the microstructured surface.

In some embodiments, the substrate may include a plurality of first level microfeatures. The first level microfeatures may have a height of 10 to 1000 microns, a diameter of 10 to 1000 microns, and a center-to-center pitch of adjacent microfeatures of 25 to 10,000 microns. In some embodiments, the substrate may further include a plurality of second level microfeatures hierarchically disposed about the first level microfeatures. In some embodiments, the second level microfeatures may include a height of 5 to 200 microns, a diameter of 5 to 200 microns, and a center-to-center pitch of adjacent microfeatures of 10 to 1000 microns. In some embodiments, the substrate may further include a plurality of third level microfeatures hierarchically disposed about the second level microfeatures. In some embodiments, the third level microfeatures may include a height of 1 to 5 microns, a diameter of 5 to 200 microns, and a center-to-center pitch of 10 to 1000 microns.

In some embodiments, the substrate may include a plurality of first level microfeatures. The first level microfeatures may have a height of 50 to 1000 microns, a diameter of 50 to 1000 microns, and a center-to-center pitch of adjacent microfeatures of 100 to 10,000 microns. In some embodiments, the substrate may further include a plurality of second level microfeatures hierarchically disposed about the first level microfeatures. In some embodiments, the second level microfeatures may include a height of 10 to 200 microns, a diameter of 10 to 200 microns, and a center-to-center pitch of adjacent microfeatures of 50 to 1000 microns. In some embodiments, the substrate may further include a plurality of third level microfeatures hierarchically disposed about the second level microfeatures. In some embodiments, the third level microfeatures may include a height of 1 to 5 microns, a diameter of 10 to 200 microns, and a center-to-center pitch of 100 to 1000 microns.

In some embodiments, the substrate may include a plurality of first level microfeatures having a height of 100 to 750 microns, a diameter of 50 to 500 microns, and a center-to-center pitch of adjacent microfeatures of 100 to 1000 microns. In some embodiments, the substrate may further include a plurality of second level microfeatures hierarchically disposed about the first level microfeatures having a height of 25 to 100 microns, a diameter of 25 to 100 microns, and a center-to-center pitch of adjacent microfeatures of 50 to 500 microns. In some embodiments, the substrate may further include a plurality of third level microfeatures hierarchically disposed about the second level microfeatures. In some embodiments, the third level microfeatures may include a height of 1 to 5 microns, a diameter of 10 to 100 microns, and a center-to-center pitch of 10 to 100 microns.

In some embodiments, the substrate may include a plurality of first level microfeatures having a height of 100 to 500 microns, a diameter of 100 to 500 microns, and a center-to-center pitch of adjacent microfeatures of 100 to 750 microns. In some embodiments, the substrate may further include a plurality of second level microfeatures hierarchically disposed about the first level microfeatures having a height of 25 to 100 microns, a diameter of 25 to 100 microns, and a center-to-center pitch of adjacent microfeatures of 50 to 500 microns. In some embodiments, the substrate may further include a plurality of third level microfeatures hierarchically disposed about the second level microfeatures. In some embodiments, the third level microfeatures may include a height of 1 to 5 microns, a diameter of 10 to 100 microns, and a center-to-center pitch of 10 to 100 microns.

In certain embodiments disclosed herein, the microstructured surface may be a microstructure pattern impressed in the first bonding material residing on one side of the fibrous layer. In some embodiments, the implantable device may include applying bonding material in a fine, spaced-apart pattern to one side of the fibrous layer and adhering a surgical mesh, and on the opposite side of the fibrous a microstructure pattern is embossed.

In some embodiments, each surface region may include bonding material. In certain embodiments, the bonding material may be elastomeric. In certain embodiments, the elastomeric bonding material may be disposed throughout the fibrous layer, or at least portions thereof, to bond the fibers into a strong network and impart abrasion resistance to both sides of the fibrous layer. In some embodiments, one side may be formed or bonded to a mesh and the other side may be formed or bonded to a microstructured surface.

In some embodiments, one side of the fibrous layer with a bonding material may be disposed in a fine, spaced-apart pattern leaving a substantial portion of that surface without bonding material. In some embodiments, the substantial portion of the surface without bonding material may be at least 40 percent or more, more preferably 50 percent or more. In such embodiments with a substantial portion without bonding material, the fibrous layer therefore provides very absorptive areas through which moisture can readily pass into the interior of the fibrous layer. In some embodiments, both sides of the fibrous layer may include a bonding material disposed in a fine, spaced-apart pattern leaving a substantial portion of both sides of the fibrous layer without bonding material. In some embodiments, the substantial portion of the surface without bonding material may be at least 40 percent or more, more preferably 50 percent or more. In such embodiments with a substantial portion without bonding material, the fibrous layer therefore provides very absorptive areas through which moisture can readily pass into the interior of the fibrous layer.

In some embodiments as disclosed herein, the central core region 310 may include a soft, relatively low-density network of fibers held loosely together by electrospun bonds or deposited during electrospinning. In some embodiments, additional strength may be imparted to the central region by the intertwining of relatively longer fibers, synthetic or natural, added to the fiber mixture of relatively shorter fibers disclosed above. The longer fibers may be provided such that the overall density of the fiber mixture is 50% or more, 60% or more, 70% or more, 80% or more, 90% or more, 95% or more, 96% or more, 97% or more, 98% or more, or 99% or more of the shorter fibers. In some embodiments, the inclusion of relatively longer fibers may be the sole strength imparted to the central region. For clarity, when referring to relatively longer fibers, it is meant that the longer fibers are at least 1.5× the length of the short fibers, or at least 2.0× the length of the short fibers, or at least 2.5× the length of the short fibers, or at least 3.0× the length of the short fibers, or at least 3.5× the length of the short fibers, or at least 4.0× the length of the short fibers, or at least 4.5× the length of the short fibers, or at least 5.0× the length of the short fibers, or at least 10.0× the length of the short fibers, or at least 20.0× the length of the short fibers, or at least 30.0× the length of the short fibers, or at least 4.0× the length of the short fibers, or at least 50.0× the length of the short fibers, or at least 100.0× the length of the short fibers.

In some embodiments, the central core region may include distinct areas, or portions, that include caverns positioned along the core region throughout. In some embodiments, these distinct areas or portions of caverns may provide additional characteristics to the core region. For example, additional characteristics may include greater bulk, softness, and absorbency to the fibrous layer. In some embodiments, separating the distinct areas from each other may include networks of fibers connecting the microstructured surface and mesh together. This embodiment may allow for constructing the implantable devices without the use of undesirable stiff adhesives as has been used in the prior art.

In some embodiments, the fibrous layer may have an undulating appearance due to patterning of the fibrous layer through use of the patterned applied bonding material. The controlled pattern of the fibrous layer may increase its bulk and absorbency, as well as its softness and compressibility.

Another embodiment of the present disclosure may include heating a surgical mesh and impress into the fibers of the surgical mesh a microstructure pattern. Heating the mesh fibers by means of a hot mandrel is not satisfactory because if the mandrel is too hot or was applied for a longer period than was necessary, it is likely to degrade the mesh tensile strength. In extreme cases, too hot an iron may melt or otherwise spoil the mesh rendering it unusable for implantation or general use.

It is one object, therefore, of this disclosure to provide an improved method of, and apparatus for, continuously impressing a pattern on materials which is free from the defects and disadvantages hereinbefore mentioned. In some embodiments, an improved method and apparatus is disclosed in which the heat to be used in the softening of a material and the period for which it is applied may be adequately controlled, and in which spoilage of material is prevented.

According to some embodiments of the present disclosure, the conveyor system, or similar system, which may feed a substrate between a cylindrical embossing roller and pressure roller or gas pressure, may further include a pair or pairs of electrodes which are connected to a source of high frequency electrical energy. Because of dielectric losses, the substrate, or portions of the substrate, may be uniformly heated rather than only superficially heated to the temperature required for impressing a microstructure onto a polymeric layer. The application of slight pressure completes the microstructure transfer process from mold to fabric.

This method and apparatus enable the operator to maintain a degree of control far superior to any which is obtainable by methods known to the prior art, i.e., convection heating, radiant heating, and/or contact heating.

Figure 4:
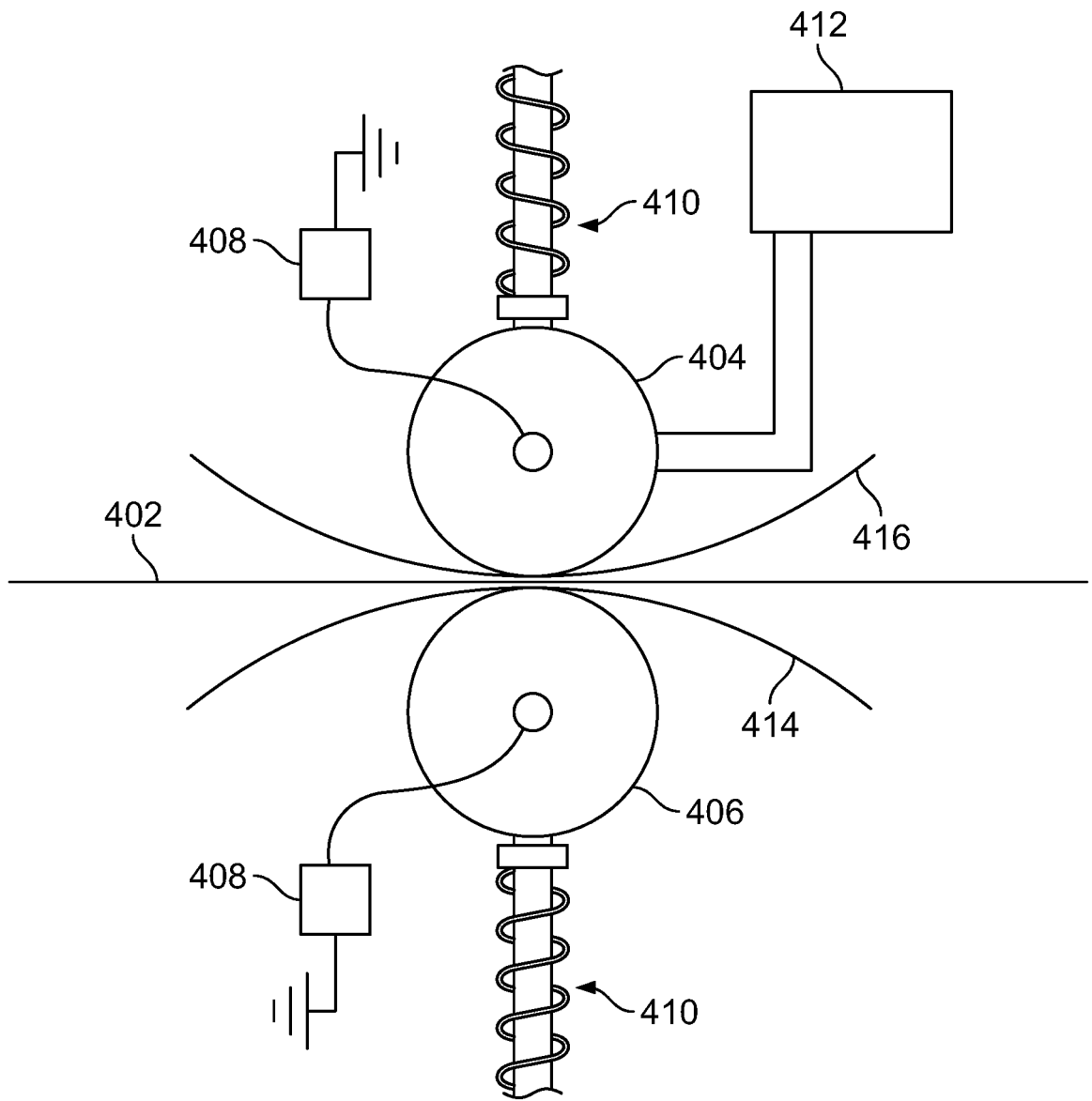
FIG. 4 is an illustration of a heating method for heating and embossing a microstructure onto a soft tissue device.

Referring now to FIG. 4, a substrate material 402 is fed along a conveyor system, or similar transport/manufacturing system, between a pair of rotating circular electrodes 404, 406. In some embodiments, the pair or rotating circular electrodes 404, 406 may be powered by RF source 408. The electrodes may be biased mechanically by a spring 410 which biases the electrodes toward each other whereby pressure is exerted upon the substrate as it passes between them.

The electrodes may be located near the point where the substrate enters the conveyor system, or otherwise as close to the point of where the fabrication process begins as may be convenient. In some embodiments, there will be two pairs of electrodes, each pair adapted to receive one side of the transported substrate sheet.

In one embodiment as depicted in FIG. 4, one of the electrodes 404 of the pair may be rotated by a motor 412 which is connected through a reduction gear, a universal joint and/or an insulated coupling. In some embodiments, the second electrode 406 of the pair may also be connected through an insulated coupling, a universal joint, and/or through a reversing gear which is connected to the motor 412 through a gearbox.

It will be understood that embodiments with two electrodes must rotate in opposite directions. In some embodiments, the electrode system may further include heat insulating belts 414, 416. The belts 414, 416 may act as a driving means for feeding the material to be treated. However, in certain embodiments, the electrodes may be stationary or freely rotating and other motor driving units may drive the substrate with respect to the electric field.

As further shown in FIG. 4, each pair of electrodes may include an associated pair of belts 414, 416. In some embodiments, these belts may be made of Teflon or other heat insulating material. They may be held on idler rollers. The belts 414, 416 may be interposed between each surface of the substrate 402 electrodes 404, 406. The belts may insulate the electrodes so that the electrode temperatures will not be unduly raised as the substrate is heated. In some embodiments, if the belts are omitted, the electrodes, because of their contact with the heated substrate, would gradually become excessively heated.

When the temperature of the electrodes is raised too high, the substrate may become tacky and may stick to the electrodes in the absence of the belts. It is this surface transfer of heat which may create a layer in the substrate where damage to the polymeric material occurs, and its tensile strength decreases.

In order that the power, which is applied through the belts, should not heat the belts, they may preferably be made of a material having very low dielectric losses. The material chosen for the buffer layer may be a dielectric such as PTFE, polypropylene, silicone, and/or polyamide. These materials all have low dielectric loss, which prevents them from heating in the RF field. These dielectrics also tend to have high breakdown voltage limits as well.

The belts, having contact with the uniformly heated substrate, may be heated by such contact. The belts may quickly begin to radiate such heat, if they are made relatively long and are exposed so that the heat is not confined. If shorter belts are required because of space limitations, their radiation may be increased by directing an air stream or other coolant on the belts.

It should be understood that belts may include any desired microstructure pattern which may be impressed upon the heated target material. Because of the uniform heating, the microstructure pattern is faithfully transferred in absence of surface effects.

In some embodiments, the electrodes may be connected to an oscillator or other source of high frequency electrical energy. Frequencies of from 200 to 300 megahertz have been found practical for this application, though the operation is not limited to those frequencies. However, if such frequencies are employed, it is possible to keep the voltage applied to the electrode within convenient limits, so that the possibility of voltage breakdown is eliminated.

High frequency electric energy from the oscillator may establish an electric field between the electrodes. The substrate passing between the electrodes, because of the dielectric losses of the material, becomes uniformly and quickly heated.

The following are examples of materials and patterns useful in practicing the disclosure given herein but are not meant to be limiting.

Example 1

A Microstructured Surface

Figures 5A, 5B:
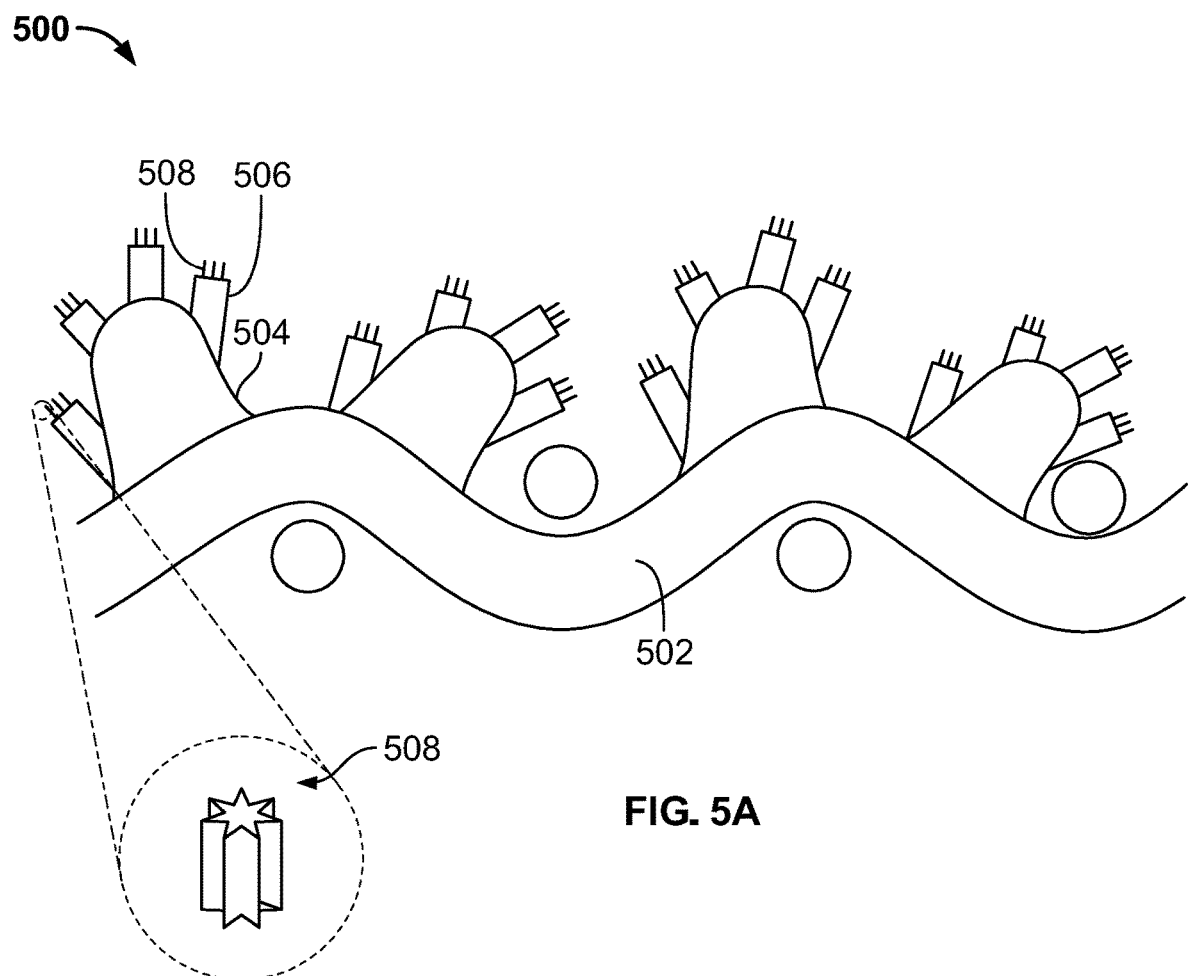
FIGS. 5A and 5B are an illustration of one embodiment of a microstructured soft tissue device.

Referring to FIG. 5, a microstructured surface 500 is disclosed which may include a substrate 502. The substrate 502 may include a first sinusoidal microstructure 504, second pillar microstructure 506 disposed on the sinusoidal microstructure, and third fluted microstructure 508 disposed on the second pillar microstructure. Each of the three different microstructures are arranged hierarchically. The diameter, pitch, and height for each of the microstructures may be defined as follows. The first sinusoidal microstructure dimensions are 1.1× to 10× the dimensions of the second pillar microstructure dimensions. The second pillar microstructure dimensions may be 1.1× to 10× the dimensions of the third fluted microstructure dimensions. The second pillar microstructures can have any elliptical or polygonal cross section.

Example 2

Mesh Coating a Microstructure Prepolymer

In certain embodiments, microstructures can be formed in polymers which crosslink to a fixed shape or are swellable. Swelling microstructures may have the added advantage of actively engaging a target surface, such as tissue, as the microstructure swells.

Poloxamer and Polylactic Acid Based Hydrogel

Pluronic 31R1 (molecular weight 3250) (BASF, Mt. Olive, NJ) was dried under vacuum at 85° C. for 12 hours in a spherical flask. The final water content obtained was below 300 ppm. One equivalent of Pluronic 31R1 was added to ⅕ equivalent (1)-Lactide and 0.18 grams catalyst (stannous 2-ethyl hexanoate) (0.43%). The reaction was carried out in a sealed flask, under a dry nitrogen saturated atmosphere, for two and half hours at 145° C.

To the above synthesis is added 2 equivalents of toluene diisocyanate and reacted at 60° C. for 8 hours. To this result is added ½ equivalent of a biofunctional molecule, for example a boswellia extract and reacted at 75° C. for 8 hours.

A hydrogel of desired viscosity is formed by adding appropriate amounts of water. For example, for a high viscosity gel, 1 g water may be added. For a low viscosity gel, 100 g of water may be added.

A mesh coated with the above prepolymer can be cured in a high humidity chamber or lightly sprayed with water.

Example 3

Polyethylene Glycol and Polylactic Acid Base Hydrogel

Polyethylene glycol ("PEG") (molecular weight 3000) was dried in vacuo overnight at 85° C. Thereafter, the PEG was cooled to room temperature and the product capped with dry nitrogen. One equivalent of PEG was added to ⅕ equivalent (1)-Lactide and 0.18 grams catalyst (stannous 2-ethyl hexanoate). The mixture of PEG and lactide was placed in an oil bath under flowing nitrogen at 140° C. and mixed for 3 hours.

To the above synthesis is added 2 equivalents of toluene diisocyanate and reacted at 60° C. for 8 hours. To this result is added ½ equivalent of a biofunctional molecule, for example a boswellia extract and reacted at 75° C. for 8 hours.

A hydrogel of desired viscosity is formed by adding appropriate amounts of water. For example, for high a viscosity gel, 1 g water may be added. For a low viscosity gel, 100 g of water may be added.

Example 4

Poloxamer and Polylactic Acid-Based Healing Hydrogel

In a reactor equipped with a stir rod, 2 moles of diisocyanate are provided under nitrogen. The reactor may be heated to 60° C. and 1 mole of poloxamer diol was slowly added. The poloxamer should be added at a rate slow enough such that the volume temperature does not rise above 65° C. If the poloxamer is a solid at 60° C., then a solvent can be used. When all the poloxamer has been added to the reaction volume the mixture should be reacted until the isocyanate content corresponds to two available NCO groups per poloxamer molecule. Adding the poloxamer slowly ensures each poloxamer molecule is endcapped with two diisocyanate molecules because the majority of the reaction is done in an excess of diisocyanate, and chain extension of the poloxamer is less probable. If prevention of chain extension is important a large excess of diisocyanate can be employed, and the excess diisocyanate evaporates at the termination of the reaction.

Once the poloxamer diisocyanate is prepared as described above, 1 mole can be loaded into a reactor under nitrogen, heated to 85° C. and two moles of dilactide (A) or more generally an ester added slowly, and as before preventing an excessive exotherm.

To this result is added ½ equivalent of a biofunctional molecule, for example a boswellia extract and reacted at 75° C. for 8 hours.

A hydrogel of desired viscosity is formed by adding appropriate amounts of water. For example, for a high viscosity gel, 1 g water is added. For a low viscosity gel, 100 g of water is added.

Thus, although there have been described particular embodiments of the present invention of a new and useful MICROSTRUCTURED SOFT TISSUE MESH it is not intended that such references be construed as limitations upon the scope of this invention except as set forth in the following claims.

What is claimed is:

1. An implantable device for repairing soft tissue comprising:
    a first substrate including a mesh;
    a second substrate having a microstructured surface; and
    a fibrous layer disposed between the first substrate and second substrate wherein the fibrous layer comprises a plurality of randomly oriented fibers.

2. The implantable device of claim 1, wherein the microstructured surface comprises a plurality of first level microfeatures and a plurality of second level microfeatures wherein at least a portion of the plurality of second level microfeatures are disposed hierarchically on at least a portion of the first level microfeatures.

3. The implantable device of claim 2, wherein the plurality of first level microfeatures have a height of 10 to 1000 microns, a diameter of 10 to 1000 microns, and a center-to-center pitch of adjacent microfeatures of 25 to 10,000 microns.

4. The implantable device of claim 3, wherein the plurality of first level microfeatures comprise a sinusoid waveform.

5. The implantable device of claim 2, wherein the plurality of second level microfeatures have a height of 5 to 200 microns, a diameter of 5 to 200 microns, and a center-to-center pitch of adjacent microfeatures of 10 to 1000 microns.

6. The implantable device of claim 2, wherein the microstructured surface further comprises a plurality of third level microfeatures wherein at least a portion of the plurality of third level microfeatures are disposed hierarchically on at least a portion of the second level microfeatures.

7. The implantable device of claim 6, wherein the plurality of third level microfeatures include a height of 1 to 5 microns, a diameter of 5 to 200 microns, and a center-to-center pitch of 10 to 1000 microns.

8. The implantable device of claim 1, wherein the second substrate is bioabsorbable and the first substrate is non-absorbable.

9. The implantable device of claim 8, wherein the mesh of the first substrate comprises polypropylene.

10. The implantable device of claim 1, wherein a first bonding material is disposed between the fibrous layer and the first substrate, a second bonding material is disposed between the fibrous later and the second substrate, the first and second bonding material bonding the first substrate and second substrate together via the fibrous layer.

11. An implantable device for repairing soft tissue comprising:
    a fibrous layer comprising a plurality of fibers wherein the fibrous layer includes a first side and an opposing second side, the first side having coated thereon a first polymer, the first polymer penetrating the fibrous layer from 10 to 60 microns and wherein the first polymer further comprises a microstructure pattern capable of generating a Wenzel-Cassie adhesive force for fixating the implantable device to a target surface.

12. The implantable device of claim 11, wherein a bonding material is disposed about the opposing second side of the fibrous layer, the bonding material contacting a mesh substrate and adhering the mesh substrate to the fibrous layer.

13. The implantable device of claim 12, wherein the bonding material penetrates the fibrous layer from 10 to 60 microns.

14. The implantable device of claim 13, wherein the first polymer and the bonding material do not contact one another within the fibrous layer.

15. The implantable device of claim 12, wherein the polymer is bioabsorbable and the mesh substrate is non-absorbable.

16. The implantable device of claim 11, wherein the microstructure pattern comprises a plurality of first level microfeatures and a plurality of second level microfeatures wherein at least a portion of the plurality of second level microfeatures are disposed hierarchically on at least a portion of the first level microfeatures.

17. The implantable device of claim 16, wherein the plurality of first level microfeatures have a height of 10 to 1000 microns, a diameter of 10 to 1000 microns, and a center-to-center pitch of adjacent microfeatures of 25 to 10,000 microns.

18. The implantable device of claim 16, wherein the plurality of second level microfeatures have a height of 5 to 200 microns, a diameter of 5 to 200 microns, and a center-to-center pitch of adjacent microfeatures of 10 to 1000 microns.

19. The implantable device of claim 11, wherein the fibrous layer comprises a plurality of randomly oriented shorter fibers deposited by electrospinning.

20. The implantable device of claim 11, wherein the fibrous layer comprises a plurality of randomly oriented shorter fibers and a plurality of longer fibers wherein the longer fibers are at least 2.0 times the length of the plurality of shorter fibers, and wherein the longer fibers constitute at least 50% or more of the overall density of the fibrous layer.

* * * * *